United States Patent [19]

Zappia

[11] 4,042,698
[45] Aug. 16, 1977

[54] TREATMENT OF MYASTHENIA GRAVIS AND ORAL MEDICATION THEREFOR

[76] Inventor: Joseph Francis Zappia, 118 N. Gibson St., Indianapolis, Ind. 46219

[21] Appl. No.: 597,302

[22] Filed: July 18, 1975

Related U.S. Application Data

[63] Continuation of Ser. No. 357,657, May 7, 1973, abandoned, which is a continuation of Ser. No. 75,277, Sept. 24, 1970, abandoned.

[51] Int. Cl.$^2$ .......................................... A61K 31/475
[52] U.S. Cl. ................................................... 424/262
[58] Field of Search ........................................ 424/262

[56] References Cited

PUBLICATIONS

Chem. Abst. I-31 — p. 8685$^4$ (1937).
Chem. Abst. II-36 — p. 7135$^2$ (1942).
Current Therapy, (1963), p. 519, W. B. Saunders Corp., Phila. and London.
Perlstein et al., American Journal of Diseases of Children, 85-(1953),pp. 56-57.

Primary Examiner—Stanley J. Friedman

[57] ABSTRACT

A human being having the medical condition known as myasthenia gravis is treated by administering at least an effective amount of strychnine to ameliorate the symptoms of the condition but less than an amount which causes persistent fasciculation of the facial muscles of the human being. The amount of medication given is balanced against the body condition safely and easily by the skilled physician. Daily dosage rates, typically, range from about 1/6000 grain of strychnine, usually as the sulfate, per kilogram of body weight to as high as about 1/300 grain or more for the more severely afflicted, i.e., into the normally fatally toxic range, usually in the form of a 1/60 grain tablet administered at the rate of 1 to 3 tablets every 2 to about 16 waking hours as needed according to the severity of the condition. Mild cases are treated intermittently while severe cases require substantially daily treatment. Vitamin B complex co-administration maximizes the effectiveness of the strychnine and tends to diminish strychnine requirements, although no side reactions of strychnine have been observed. Strychnine requirements may also be reduced by co-administering deanol or neostigmine bromide or the dimethylcarbamate of 3-hydroxy-1-methylpyridinium.

8 Claims, No Drawings

TREATMENT OF MYASTHENIA GRAVIS AND ORAL MEDICATION THEREFOR

CROSS-REFERENCE TO RELATED APPLICATIONS

This is a continuation of application Ser. No. 357,657, filed May 7, 1973 which is in turn a continuation of application Ser. No. 75,277 filed Sept. 24, 1970 both are now abandoned.

BACKGROUND OF THE INVENTION

1. Field of the Invention

The invention relates to an improved method for the treatment of the human medical condition known as myasthenia gravis.

For the purposes of the following description and the appended claims, myasthenia gravis is defined as a condition typified by a fluctuating condition of easy fatigability of voluntary muscles aggravated by exertion, emotion, menstruation or infection, and relieved, both subjectively and objectively, by rest and anticholinesterase drugs. The patient with a so-called mild myasthenia gravis condition generally needs treatment on an intermittent basis as the condition worsens and improves spontaneously in an intermittent manner. The patient with a seriously marked or severe myasthenia gravis condition generally requires treatment on a regular conditioning basis, usually daily.

Myasthenia gravis is a problem probably more widespread than heretofore realized for in the past only the more advanced or severe stages of the condition were recognized and labeled as myasthenia gravis. By ergograms and "Tensilon Tests" rather recently developed we have learned that there can be different degrees of the disease manifesting a variety of symptoms. Moderately servere symptoms can be and often are mistaken for psychological disorders. Not only is the myasthenia gravis patient (myasthenic) not helped by treatment for psychological disorder but suffers more as a result. In the not too severe cases, the condition may be wrongly assessed psychologically as a withdrawal from normal interests and activities.

2. Description of the Prior Art

Several drugs are currently in use, including neostigmine bromide and the dimethylcarbamate of 3-hydroxy-1-methylpyridinium. Although these drugs are of some help, they have many disadvantages. Satisfactory dosage regimens are hard to determine because the drugs are so powerful and coordination with body needs and utilization is difficult if not impossible since the drugs seem never to quite match the imbalance in the body and satisfy its requirements. As a result, overdosages as well as underdosages occur, much to the discomfort of the myasthenic. Moreover, these drugs are so inherently dangerous that the patient under treatment therewith must carry atropine, as 1/120 grain tablets, as an antidote immediately available to overcome accidental or incidental overdosage.

For the myasthenic with a severe condition, huge quantities of the drugs in current use are often necessary, which can only be taken if the patient tolerates the drugs at that level. For example, one of the drugs has been given at a level as high as 72 60 milligram tablets dialy over an extended period. Because each of the currently used drugs cause substantial side reactions the patient is not truly comfortable with such drugs at any dosage level.

OBJECTS OF THE INVENTION

The principal object of the invention is to provide a method of treatment of myasthenia gravis which provides for from substantial amelioration to complete remission of the condition for at least transitory periods and can be easily and safely used in good control on a long term basis, if necessary.

Another object of the invention is to overcome the many problems which heretofore have not been solved by the use of the drugs presently available for the treatment of myasthenia gravis.

A further object of the invention is to provide a simple inexpensive method of treating myasthenia gravis with a drug far cheaper than any in current use for the condition.

A specific object of the invention is to provide a method of treatment of myasthenia gravis which is relatively safe in the hands of the trained medical practitioner in that overdosing is easily detected and avoided.

A further object of the invention is to provide a relatively safe but effective oral medication for the treatment of myasthenia gravis which medication substantially perfectly meets the needs of the body condition and substantially does not cause adverse side reactions or changes in blood chemistry.

These and other objects and advantages of the present invention will be more fully understood by those skilled in the art upon becoming familiar with the following description and the appended claims.

STATEMENT OF THE INVENTION

It has now been surprisingly discovered that the administration of strychnine in pharmaceutically acceptable oral form to a myasthenia gravis patient in, what is for such patient, an effective amount but less than the amount which causes fasciculation of the facial muscles, during periods of needed treatment for the condition, brings about substantial elimination of the symptoms of myasthenia gravis during and sometimes after such treatment, including elimination of the characteristic rapid fatigue of muscles, and such relief is obtained substantially without side effects or changes in blood chemistry. Patients with a mild form of the condition, after one to several days or more of treatment, typically, will experience periods of several days or more, from time to time, when they are able to discontinue treatment until the condition again spontaneously worsens. Patients with a serious case will generally require substantially daily use of the drug.

BRIEF DESCRIPTION OF THE INVENTION

For the purposes of the description and the appended claims, the term strychnine includes the pharmaceutically acceptable salts of strychnine which are readily water soluble acid addition salts in which the anion of the acid used to form such salt is substantially not toxic to the human patient at the dosage levels normally employed for the solubilized salt. Typically, strychnine is used as the acid addition salt of hydrochloric acid or sulfuric acid. The acid addition salt of nitric acid is also usable if available.

The method of the invention is carried out by administering strychnine in an effective amount, generally at least 1/6000 grain of the salt per kilogram of body weight (gr./kg.) per day, and more generally at least 1/3000 gr./kg. per day, but always less than the amount which causes fasciculation or twitching of the facial muscles in the patient under treatment. Generally not more than about 1/300 gr./kg. per day total is required for a patient with a more severe condition. Such a level is highly toxic or fatal to the normal non-myasthenic human subject as well as to the myasthenic with a mild condition and even the myasthenic with a severe condition must not take the needed daily amount in one dose, but must spread out administration of the drug at a rate of not more than about 3/60 grain every 2 to 4 hours.

In a conservative course of treatment an average adult with a relatively mild myasthenic condition is treated with 1/60 grain of strychnine salt per day for about 3 to 4 days. If the symptoms of the condition are adequately alleviated, dosage is continued at the same rate on those days when it appears to be needed. However, if the symptoms of myasthenia gravis are not completely ameliorated, the dosage is increased to about 1/40 grain per day for the next 3 to 4 days, after which, if that is not enough, the dosage is further increased to 1/30 grain per day for several days, and so on, until the usual daily dose for the patient is determined, care being taken at all times to back off from the dosage level which causes twitching of facial muscles, the latter being a prompt and reliable indicator of slight overdosing.

In the hands of the trained physician and in a safe controlled environment such as that of a patient confined to a hospital or clinic, substantially complete elimination of the symptoms of the myasthenia gravis condition is readily, promptly and safely obtained by administering, initially, about 1/3000 gr./kg., or more typically, one to three 1/60 grain tablets, of strychnine salt about every 3 hours until fasciculation of the eyelids or other facial muscles is detected or observed, after which the dosage to be taken during waking hours is reduced by about 1/6000 gr./kg., or, the time interval between doses is increased by one to three or more hours.

Waking hours here means the period of time from normal rising to normal bedtime for the patient.

It is also to be understood that strychnine may be given in parenteral form by injection, if desired, to overcome the symptoms of myasthenia gravis, in a manner similar to that described above in approaching carefully the level of slight overdosing and then reducing the dose slightly. However, oral administration is so simple and effective that few patients would find the injection route desirable.

The most effective but safe dosage, for a badly afflicted individual, may well be at a level which is lethal to a human subject who does not have the myasthenia condition. Dosage levels for individual myasthenic patients are determined in the manner described, which amounts to a balancing or titrating of the drug against the patient's myasthenia gravis condition. Unless the dosage level selected brings or fasciculation of the facial muscles, administration of strychnine is continued on a long term basis in an intermittent manner or daily pattern according to need in which at least one day of administration of strychnine is followed by at least one day of non-administration of the drug. For the more severe cases there is seldom a period of spontaneous remission and administration of strychnine is carried out substantially every day to keep the patient comfortable at all times.

The treatment is remarkable for the marked absence of discernible side effects or changes in blood chemistry or other body conditions on chronic dosing, nor are increased dosage levels required for long term maintenance medication.

In all cases, it is highly advisable that treatment be initiated under the observation of a qualified medical doctor and that the patient remain under the doctor's care.

Since indiviual needs may vary considerably and even from day to day or week to week in the same subject, it must be understood that dosages as high as about 1/300 gr./kg. or sometimes even more per 16 hour period, may be required to fully alleviate the symptoms of the grave myasthenic condition, usually not more than 3 1/60 grain tablets being taken initially and about every 2 to 4 hours thereafter during waking hours. Treatment is almost never needed at bedtime or during sleep periods by the true myasthenic.

Strychnine is normally supplied as strychnine sulfate in tablets of 1/30 grain, 1/40 grain, and 1/60 grain dosage. The drug blended with standard excipients may also be made up in capsule form. Strychnine is also readily prepared in the form of aqueous and alcoholic solutions. It can also be prepared with other vehicles, especially orally acceptable vehicles, provided that incompatibilities inherent to the drug are observed at all times.

In another embodiment of the invention, strychnine salt is administered in conjunction with the psychic energizer, 2-dimethyl-aminoethanol as the p-acetamidobenzoic acid salt. This latter material is supplied by Riker Laboratories, Inc., under the brand name Deaner as tablets each containing 25 milligrams of the active ingredient.

The psychic energizer is given in partial substitution for the strychnine salt and reduces the requirements therefor in treating myasthenia gravis. Typically, a 25 milligram quantity of the psychic energizer is substituted for a 1/60 grain tablet of the strychnine salt where from 2 to 3 such tablets of the strychnine salt are indicated, although a lesser proportion of the psychic energizer may be administered if desired.

A novel and useful drug combination prepared for the benefit and convenience of the myasthenic contains the said Deaner psychic energizer and the strychnine salt combined in a pharmaceutically acceptable dosage form suitable for oral administration. Suitable dosage forms include elixirs, tablets and capsules, including sustained release formulations made up into tablets or used to fill capsules according to the methods of and using the materials of U.S. Pat. Nos. 3,133,863, 2,793,979 and 2,853,420, the disclosures of which are incorporated herein by reference. In any event, a suitable dosage form is readily accepted by the patient and provides the desired amount of medication, per unit dose, i.e., per spoonful or tablet or capsule. In making up tablets of the drug combination, the psychic energizer material and the strychnine salt are physically blended together along with one or more standard tabletting excipients, e.g., starch, and granulated and blended with, e.g., magnesium stearate and talc and tabletted as well understood in the art. On the other hand, the psychic energizer material and the strychnine salt may be simply blended together with or without suitable and compatible standard inactive diluents or excipients necessary to make up the requisite capsule voleume and encapsulated in gelatin capsules.

The psychic energizer material and the strychnine salt are combined in proportions ranging from about 25 milligrams of the psychic energizer material per 1/240 to 1/15 grain of strychnine salt, but more usually at a ratio of about 25 milligrams of psychic energizer material to from 1/60 to 1/20 grain of strychnine salt.

In a preferred embodiment of the invention, the strychnine salt, with or without being combined with the psychic energizer material, is administered in conjunction with or physically admixed with vitamin B complex preparations such as Becotin(Lilly), Becotin T(Lilly), Becotin with Vitamin C(Lilly) or Squibb vitamin B complex, or equivalent commercial vitamin B complex preparations. Such preparations normally contain thiamine hydrochloride, riboflavin, pyridoxine hydrochloride, nicotinamide, calcium pantothenate, vitamin $B_{12}$ active material, liver preparation, and stomach-tissue material, desiccated (extrinsic factor).

Administration of at least sufficient vitamin B complex to assure that the patient has received, about every day, minmum daily requirements of the various B vitamins, where established, or, if not, typically recommended doses for vitamin supplementation, is indicated to cause the patient to have a marked feeling of well being and to have a tendency to exhibit a reduced need for strychnine salt.

Generally, the patient should receive from about one-half to ten times the minimum daily requirement for each of the B vitamins, and preferably one and one-half to four times the minmum daily requirement.

Another novel and useful drug combination for the benefit and convenience of the myasthenic contains vitamin B complex and strychnine salt with or without Deaner psychic energizer (deanol salt). The vitamin B complex is used in sufficient amount to provide about 0.5 to 10 times the minimum daily requirement of B complex vitamins per prospective daily dose of strychnine salt, i.e., from about one-sixtieth to one-fourth grain of the salt. The unit dose is generally prepared with about 0.5 to 10 times the minimum daily requirement of B complex vitamins per one-two hundred fortieth to one-fifteenth grain of strychnine salt and more preferably 1.5 to 4 times the minimum daily requirement per prospective daily dose of strychnine salt, which is often in the range of 1/60 to 1/20 grain for treating mild to moderately severe cases.

When deanol salt is combined with the foregoing combination, it is generally combined in a ratio of about 100 milligrams of deanol salt per one-sixtieth to four-fifteenths grain of strychnine salt. In unit dosage forms, about 25 milligrams of deanol salt is employed per one-two hundred fortieth to one-fifteenth grain of strychnine salt.

In other novel and useful combinations of medication according to the invention strychnine salt and vitamin B complex are combined with one of the heretofore conventional drugs for myasthenia gravis. In such combinations, a daily dose amount of medication contains from one-half to two-thirds or more of the indicated level of strychnine salt for a given class of patient rated according to severity of condition, i.e., from about 1/120 to about 1/12 grain, and one of about 23 to 125 milligrams of neostigmine bromide and 30 to 500 milligrams of the dimethylcarbamate of 3-hydroxy-1-methylpyridinium, in addition to 0.5 to 10 times the minmum daily requirement of the B complex vitamins.

In making up the drug combinations according to the invention in dosage form, the materials are blended with each other in the proper proportions or ratios and combined with a standard excipient, such as starch, or a suitable combination of standard excipients, and granulated, and blended with, e.g., magnesium stearate and talc, or other material for the improvement of properties during tabletting, and compressed into tablets. Also the components of the combinations may be simply blended, with or without standard excipients present such as starch, glucose, magnesium carbonate, mannitol or lactose, to achieve a desired bulk volume, and incorporated into gelatin capsules, e.g., hard gelating capsules. In selecting inert ingredients, compatibilities thereof with the compnents selected, as well as the compatibilities among the components themselves, according to standard texts such as Hussa, *Pharmaceutical Dispensing,* are best observed to assure reasonable shelf life, particularly in the combinations which include the B complex vitamins. Desirably, the several drugs and vitamins are individually granulated and even more desirably the granulated material is coated with a very light coating of a gum or wax, such as acacia, gum tragacanth, karaya gum, glyceryl monostearate, beeswax, carnauba wax, ethyl cellulose or methyl propyl cellulose, or a material like shellac, before blending the components of the combination together, particularly where the B vitamins are included. Time release compositions containing any of the described combinations may also be prepared using the techniques described in the patents referred to hereinabove.

The mode of action of the drug strychnine in the present method of treatment is not entirely understood, but it is believed that the disruption or reversal of a physiological enzyme system is effected, whereby the condition is truly corrected back to normal without causing concurrent disorder in any other system. Therefore, it may be readily seen and understood that high threshold dosages may be employed by a skilled physician in initial treatment, e.g., up to about 1/1600 gr./kg/about every three hours for severe cases, but more usually about 1/4800 gr./kg. every three hours for moderate to mild cases.

In further explanation of the suspected mode of operation, it is believed that the mechanism of the present treatment centers around the biochemistry of the myoneural junction and the attendant enzyme control system. The myoneural junction is the zone or space where a nerve bringing in a stimulus and the muscle fiber it serves closely approach but are not in physical contact and the transmission of the stimulus is effected through an electrolyte medium. The transmitted impulse causes muscle contraction. Acetylcholine present in the electrolyte medium at the myoneural junction at the time of transmission of a nerve impulse facilitates or makes possible transmission of the impulse. Acetylcholine appears to be destroyed by cholinesterase compounds during or immediately after each transmission only to be built up again in quantities sufficient to permit again, at the myoneural junction, the ideal condition for the transmission of another nerve impulse. How fast and how often this process is repeated in a period of time is unknown. It probably varies with the various muscle groups involved as well as voluntary physical motions as the individual may desire, or be required to perform.

Myasthenia gravis is the condition produced when acetylcholine is not restored to this myoneural junction at the normal rate while the formation of cholinesterase appears to proceed unabated, resulting in extremely marked inhibition of the acetylcholine part of the cycle.

Up to now the treatment of myasthenia gravis has been carried out by supplying the patient, from a source external to the body, drugs which inhibit the destruction of acetylcholine by cholinesterase and thereby permit freer transmission of nerve impulses across the neuro-muscular junction. However, these drugs, classed as anticholinesterases, leave something to be desired when administered in the hope of precisely correcting the body disfunction.

Strychnine, even though it also acts in a general way as an anticholinesterase, somehow seems to correct in an very natural direct manner whatever was lacking in the enzyme system cycle preventing the formation of sufficient acetylcholine, or the pre-cursors thereof, and preventing maintenance of a smooth proper equilibrium at the myoneural junction and normal muscle function. As a consequence, the administration of strychnine to a myasthenic is notable for the great precision with which body needs are met.

EXAMPLE 1

A white male, age 38, and weighing about 70 kilograms, with a confirmed mild to moderate myasthenia gravis condition of 4 years duration, was given a starting dose of 1/60 grain of strychnine once daily for 2 days and noted at once marked amelioration of the symptoms of the condition. Then the dose was increased to 1/60 grain twice daily for 2 days after which the dose was further increased to 1/30 grain twice daily for the next succeeding 3 days. Following the seventh successive day of treatment in this manner no more medication or other treatment was necessary for a period of sixteen weeks to avoid the occurrence of noticeable symptoms of myasthenia gravis in this patient.

Thereafter, for an extended period of over 6 years, the patient was administered strychnine sulfate as the need arose. Treatment consisted of administration of about 4 to 10 1/60 grain tablets, and more typically 6 to 8 1/60 grain tablets, daily, taken 1 to 2 every 3 to 4 hours. Treatment was continued for from 3 to 14 days at a time, in each case until myasthenia gravis symptoms subsided, and intervals between periods of treatment varied from about 1 day to about 3 weeks. The patient noted very satisfactory relief from the symptoms of myasthenia gravis throughout the entire period of over 6 years.

From time to time and at respectively different times, the patient was given vitamin B complex preparations known as Becotin(Lilly, Becotin T(Lilly), Becotin with Vitamin C (Lilly) and Squibb B complex vitamins, concurrently with administration of strychnine sulfate as described. The vitamin preparations were taken in sufficient amount to supply about 2 times the minimum daily requirement of the vitamins for which the requirement has been established. During administration of the vitamin B complex preparations, the patient noted a heightened sense of well being and a tendency for reduced requirements for the strychnine needed to overcome the symptoms of myasthenia gravis.

EXAMPLE 2

A white male, about 28 years of age and weighing about 82 kilograms, with a confirmed grave myasthenia gravis condition of a number of years duration, and with a history of unsatisfactory or uncomfortable treatment with conventional drugs for myasthenia gravis, after 72 hours without medication, was given a starting dose of one-sixtieth grain of strychnine sulfate in the form of a standard tablet crushed and deposited in a gelatin capsule. Prompt ameliotation of the myasthenia gravis condition was noted within 30 minutes as determined by prior and subsequent administration of ergogram tests.

Approximately two months later, during which time conventional myasthenia gravis drugs were administered, the patient commenced treatment according to the invention with ever increasing daily doses of strychnine sulfate until daily dosages of 2 to 3 1/60 grain tablets of strychnine sulfate were being administered about every 3 hours during waking hours. The patient, who had been unable to complete a normal work day without intervening periods of sleep, was able to maintain normal physical activity throughout a standard workday. Titration of the drug against the myasthenia gravis condition was continued substantially daily for over 20 months with substantially complete and highly satisfactory relief from the condition. Repeated blood chemistry tests showed no abnormalities in blood cell types or counts.

On one occasion during the 20 month period, the patient was given, for about a ten day period, 25 milligram tablets of a psychic energizer sold under the brand name Deaner and containing, in each tablet, 25 milligrams of the compound 2-dimethyl-aminoethanol as the p-acetamidobenzoic acid salt, a compound also known as deanol. The deanol tablets were given in partial substitution of 1/60 grain strychnine sulfate tablets, one tablet of deanol and one tablet of the strychnine salt being administered for each two tablets of strychnine requirement indicated. The partial substitution was completely satisfactory in that the patient experienced substantially the same fine relief from the symptoms of myasthenia gravis as were observed on administering strychnine sulfate alone.

The patient was also at various other times during the said 20 month period, given B complex vitamin preparations known as, respectively, Becotin T(Lilly) and Becotin with Vitamin C(Lilly). Becotin T is a high potency preparation. These preparations were, at respective times, administered along with strychnine sulfate and with and without deanol in addition, i.e., with deanol in partial substitution when used. Under these circumstances, the B complex vitamins gave the patient a markedly heightened sense of well being and tended to reduce the requirements for strychnine or the requirements for strychnine plus deanol.

I claim:

1. The method of treating a human being having the condition known as myasthenia gravis which comprises: administering strychnine to the said human being in at least an effective amount to ameliorate the symptoms of the condition but less than the amount which will cause persistent fasciculation of facial muscles of said human being.
2. The method of claim 1 wherein the amount of strychnine administered per day is at least 1/6000 grain per kilogram of body weight.
3. The method of claim 1 wherein the amount of strychnine administered per day is at least 1/6000 grain per kilogram of body weight but is not more than about 1/300 grain per kilogram of body weight, such administration being during waking hours and at a rate of not more than about 3/60 grain every 2 to 4 hours.
4. The method of claim 1 in which the strychnine is administered on a long term basis in an intermittent daily pattern according to need in which at least one day of administration of strychnine is followed by at least one day of non-administration of strychnine.
5. The method of claim 1 in which administration of strychnine is carried out substantially every day.

6. The method of claim 1 in which the strychnine is employed in the form of a pharmaceutically acceptable acid addition salt.

7. The method of claim 1 in which there is concurrently administered to said human being from about to 10 times the minimum daily requirement of the B vitamins.

8. The method of claim 7 in which the B vitamins are a mixture of substantially each of thiamin, riboflavin, pyridoxine, niacinamide, calcium pantothenate, vitamin $B_{12}$ active material, liver preparation and stomach tissue material, desiccated, in relative proportions similar to that found in the commercial vitamin B complex preparations.

* * * * *